United States Patent [19]

Chang

[11] Patent Number: 4,846,882
[45] Date of Patent: Jul. 11, 1989

[54] HERBICIDAL ARYL TETRAHYDROPHTHALIMIDES

[75] Inventor: Jun H. Chang, Princeton Junction, N.J.

[73] Assignee: FMC Corporation, Philadelphia, Pa.

[21] Appl. No.: 69,662

[22] Filed: Jul. 6, 1987

Related U.S. Application Data

[63] Continuation-in-part of Ser. No. 914,555, Oct. 3, 1986, abandoned, which is a continuation-in-part of Ser. No. 818,647, Jan. 10, 1986, abandoned.

[51] Int. Cl.$^4$ .................. A01N 43/38; C07D 209/48
[52] U.S. Cl. ........................................ 71/96; 544/144; 548/240; 548/465; 548/513
[58] Field of Search .............................. 548/513; 71/96

[56] References Cited

U.S. PATENT DOCUMENTS

| | | | |
|---|---|---|---|
| 2,192,271 | 3/1940 | Mirocourt et al. | 564/440 |
| 2,734,073 | 2/1956 | Frevel et al. | 564/213 |
| 3,299,127 | 1/1967 | Zienty | 562/452 |
| 3,313,700 | 4/1967 | Bossinger et al. | 560/163 |
| 3,366,625 | 1/1968 | Hebky et al. | 564/220 |
| 3,399,048 | 8/1968 | Herrett et al. | 560/163 |
| 3,419,620 | 12/1968 | Becher et al. | 558/482 |
| 3,856,857 | 12/1974 | Beregi et al. | 564/44 |
| 3,984,450 | 10/1976 | Fischer et al. | 558/242 |
| 3,992,189 | 11/1976 | Goddard | 71/96 |
| 4,062,978 | 12/1977 | Cole et al. | 568/586 |
| 4,098,901 | 7/1978 | Lindberg et al. | 560/173 |
| 4,168,388 | 9/1979 | Lavagnino et al. | 568/586 |
| 4,271,888 | 6/1981 | Hindley | 562/456 |
| 4,292,070 | 9/1981 | Wakabayashi et al. | 71/96 |
| 4,339,461 | 7/1982 | King | 564/99 |
| 4,386,035 | 5/1983 | Maurer et al. | 562/493 |
| 4,430,114 | 2/1984 | Lutz et al. | 71/105 |
| 4,431,822 | 2/1984 | Nagano et al. | 548/513 |
| 4,439,229 | 3/1984 | Swithenbank | 548/513 |
| 4,443,625 | 4/1984 | Griffith et al. | 560/254 |
| 4,552,585 | 11/1985 | Chang | 71/88 |
| 4,770,694 | 9/1988 | Nagano et al. | 548/513 |

FOREIGN PATENT DOCUMENTS

| | | |
|---|---|---|
| 52559 | 5/1982 | European Pat. Off. |
| 1518688 | 3/1969 | Fed. Rep. of Germany |
| 45-09935 | 4/1970 | Japan |
| 8103350 | 6/1983 | Japan |
| 881588 | 11/1961 | United Kingdom |
| 968254 | 9/1964 | United Kingdom |

OTHER PUBLICATIONS

T. Wheeler et al., Chem. Abstracts, vol. 109, No. 6409f (1988).

Primary Examiner—Mary E. Ceperley
Attorney, Agent, or Firm—Robert M. Kennedy; H. Robinson Ertelt

[57] ABSTRACT

A herbicidal compound of the formula

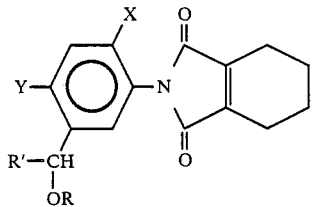

where X is F, Cl or Br, Y is Cl, Br, $CHF_2O$ or $CF_3$, R is alkyl of 1 to 6 carbon atoms or lower halo alkyl and R' is H or lower alkyl. Related compounds, including those which have —SR or —NR$^2$R in place of —OR are also disclosed.

15 Claims, No Drawings

HERBICIDAL ARYL TETRAHYDROPHTHALIMIDES

This application is a continuation-in-part of application Ser. No. 914,555, filed Oct. 3, 1986, now abandoned, which is a continuation-in-part of application Ser. No. 818,647, filed Jan. 10, 1986, now abandoned.

The invention described in this application pertains to weed control in agriculture, horticulture, and other fields where there is a desire to control unwanted plant growth. More specifically, the present application describes certain herbicidal aryl tetrahydrophthalimides, compositions of them, methods of preparing them, and methods for preventing or destroying undesired plant growth by preemergence or postemergence application of the herbicidal compositions to the locus where control is desired. The present compounds may be used to effectively control a variety of both grassy and broadleaf plant species. The present invention is particularly useful in agriculture; a number of the compounds described herein show a selectivity favorable to certain crops (e.g. soybeans, corn, rice, including paddy rice, and wheat on preemergence or postemergence treatment) at application levels which inhibit the growth or destroy the growth of a variety of weeds.

A particularly effective aspect of this invention relates to the herbicidal compound of the formula:

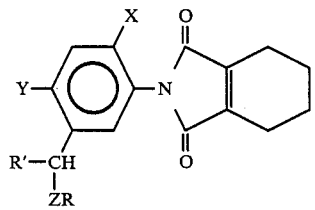

where X is F, Y is Cl, R' is H, Z is O, and R is $C_2H_5$. X may also be Cl or Br; Y may also be Br or $CHF_2O$ or $CF_3$.

Instead of ethyl, R may also be another alkyl of 1 to 6 carbon atoms (e.g., methyl, propyl, isopropyl, butyl or t-butyl); lower haloalkyl (e.g., chloroethyl or fluoropropyl); aryl (e.g., phenyl, or methoxy— or chloro-substituted phenyl); aralkyl (e.g., benzyl); alkylcarbonyl (such as lower alkyl carbonyl, e.g., $CH_3CO$— or $C_2H_5CO$—); haloalkylcarbonyl (such as lower haloalkylcarbonyl, e.g. $ClCH_2CO$—, $FCH_2CO$— or $ClCH_2CH_2CO$—); alkoxy— (or haloalkoxy—)carbonylalkyl (e.g., in which the alkoxy and alkyl moieties are each of 1 to 6 carbon atoms, such as $CH_3OC(O)CH_2$— or $C_2H_5OC(O)CH(CH_3)$— or $ClCH_2OC(O)CH_2$—); alkyl— (or haloalkyl— or aryl—)aminocarbonyl (e.g., $CH_3NHCO$—); carboxyalkyl (e.g., —$CH_2C(O)OH$); aryloxycarbonylalkyl, e.g.

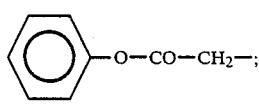

aralkyloxycarbonylalkyl, e.g.,

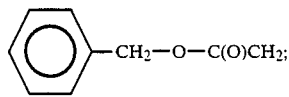

aminocarbonylalkyl (e.g., $NH_2C(O)CH_2$—); lower alkylaminocarbonylalkyl (e.g., $C_2H_5NHC(O)CH_2$—); arylaminocarbonylalkyl, e.g.,

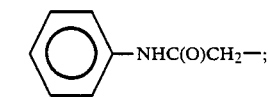

alkylsulfonylaminocarbonylalkyl (e.g., $CH_3SO_2NH$-$C(O)CH_2$); or arylsulfonylaminocarbonylalkyl, e.g.,

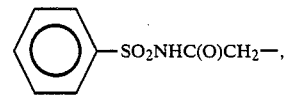

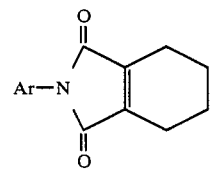

Instead of being O, Z may also be S or S(O) or $S(O)_2$, with R and R' being as described herein.

Z may also be $NR^2$ with $R^2$ being hydrogen, lower alkyl (e.g., of 1 to 6 carbon atoms such as methyl or butyl), lower alkoxy (such as methoxy), aralkyloxy (e.g., benzyloxy), or $R^2$ taken with R may be a divalent radical such as alkylene (e.g., butylene), alkylenoxyalkylene (e.g., as in compound 32 of Table 1), carbonylalkylenoxy (e.g., as in compound 33). R and R' may be as described herein.

Instead of H, R' may also be lower alkyl (e.g., of 1 to 6 carbon atoms such as methyl, ethyl, propyl or butyl).

In each aspect of the invention it is often preferable that any alkyl, alkenyl, alkynyl, or alkylene moiety (such as the hydrocarbon moiety of an alkoxy or haloalkoxy group) have less than 6 carbon atoms, e.g., 1 to 3 carbon atoms.

In a broader aspect of the invention, it relates to herbicidal compounds of the formula $$\text{(Formula II)}$$

wherein Ar is a substituted phenyl radical having the group —CH(R')ZR in its 5-position (e.g. meta to the nitrogen of said formula), with the proviso that the compound is one whose Methoxy Analog or Propargyloxy Analog is a herbicide. The term "Methoxy Analog" is used here to designate a compound which is otherwise identical to said compound of Formula II except that it has a methoxy group instead of the —CH(R')ZR group of said compound of Formula II. The term "Propargyloxy Analog" is similarly used here for a compound which is otherwise identical to said compound of Formula II except that it has a propargyloxy group instead of the —CH(R')ZR group of said compound of Formula II. Preferably, "Ar" carries a substituent (i.e. other than H) at the 2-position or the 4-position of the phenyl radical, most preferably at both the 2- and 4-positions. Also, preferably R' is H and R is ethyl.

Herbicidal aryl tetrahydrophthalimides are disclosed in U.S. Pat. Nos. 4,292,070 (which describes compounds having a 5-propargyloxy substituent on the phenyl group) and 4,431,822.

The compounds of this invention preferably have Methoxy Analogs and Propargyloxy Analogs of marked herbicidal properties. For instance, said Analogs of the preferred compounds show at least 50% kill of at least one of the following species of plants when applied under at least one of the following modes at the rate of 0.5 kg/ha, and more preferably show such kill of at least 50% when applied at the rate of 0.1 kg/ha: Species; velvetleaf (*Abutilon theophrasti*), green foxtail (*Setaria viridis*); Modes: pre-emergent, postemergent. Testing for such herbicidal activity may be carried out in the manner described below (under the heading "Herbicidal Activity").

Representative compounds of this invention are listed in Table 1 below.

The compounds of this invention may be prepared by the use of steps generally described in the literature or by methods analogous or similar thereto and within the skill of the art.

In Examples 1, 8, 9 and 10 below the starting material is a substituted benzyl bromide, e.g., of the formula

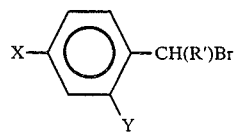

which is reacted with a nucleophile (e.g., an etherifying agent), to form, for instance, an intermediate

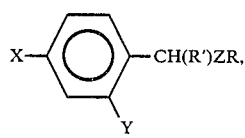

then nitrated to place an NO2 group on the benzene ring, to form, for instance, an intermediate

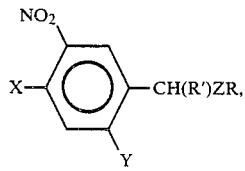

and then reduced to convert the NO2 group to an amino group to form, for instance, an intermediate

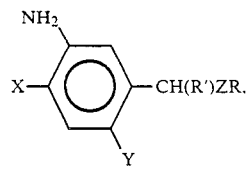

and then reacted with tetrahydrophthalic anhydride to form the imide. The nitration may precede the reaction with the nucleophile; thus in Example 7 one may start with a substituted nitrotoluene, e.g., of the formula

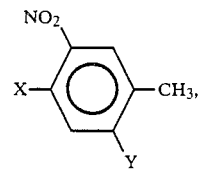

and convert the nitro group to a (protected) amino group, e.g., forming an intermediate

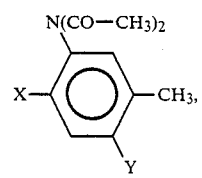

then convert to the benzyl halide, such as a benzyl bromide, e.g., forming

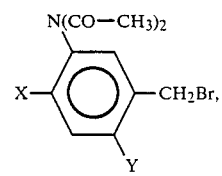

and then react with the nucleophile.

Example 2, in which R' is alkyl, illustrates a process in which there is formed a substituted benzaldehyde, e.g., of the formula

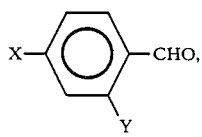

which is converted in known manner e.g., in a series of reactions involving a Grignard reagent) to the corresponding secondary alcohol, e.g.,

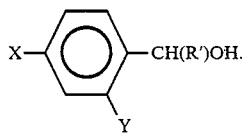

Nitration of the alcohol (under mild conditions, such as with HNO₃ in a solvent at a temperature of about −20° to 5° C.) before the reaction with the nucleophile not only places an NO₂ group on the aromatic ring but also converts the alcoholic OH group to an —ONO₂ group, forming,

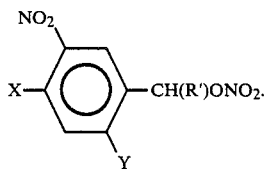

That —ONO₂ group may than be converted to, e.g., an OR group by reaction with a nucleophile such as a conventional etherifying agent, e.g., an alkali metal alkoxide.

Examples 3 to 6 illustrate a process in which the substituted benzaldehyde, e.g., of the formula

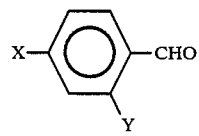

is nitrated and reduced to form the corresponding nitro alcohol,

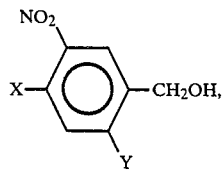

and the amino alcohol, e.g.,

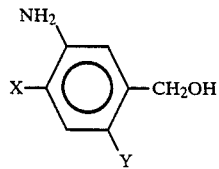

and in which the alcoholic hydroxyl is reacted, to form the desired final compound, after the imide-forming reaction with the tetrahydrophthalic anhydride.

EXAMPLE 1

Synthesis of
N-[4-Chloro-2-Fluro-5-Ethoxymethylphenyl]-3,4,5,6-Tetrahydrophthalimide

Step A

Synthesis of 2-chloro-4-fluorobenzyl ethyl ether

Tetrahydrofuran (50 ml) was added to stirred sodium hydride ( 1.26 g, 0.053 mole) under a nitrogen atmosphere while being cooled in an ice-water bath. Absolute ethanol (5 ml) was then added dropwise and the reaction stirred until hydrogen evolution ceased. A solution of 2-chloro-4-fluorobenzyl bromide (10.62 g, 0.0475 mole ) in tetrahydrofuran (10 ml) was then added to the reaction mixture. The reaction mixture was allowed to stir at ambient temperature overnight. Ethanol and tetrahydrofuran were removed under reduced pressure. The reaction mixture was diluted with diethyl ether (200 ml), washed with water (4×75 ml), dried (magnesium sulfate) and concentrated under reduced pressure to remove solvent. The residue was distilled at low pressure yielding 5.27 g of 2-chloro-4-fluorobenzyl ethyl ether, b.p. 67°–68° C./10 mm Hg. The nmr spectrum was consistent with the proposed structure.

Step B

Synthesis of 4-chloro-5-ethoxymethyl-2-fluoronitrobenzene

To a cooled (−40° C.) solution of fuming nitric acid (90%, 25 ml) was added dropwise 2-chloro-4-fluorobenzyl ethyl ether (2.5 g, 0.013 mole) at a rate which maintained the temperature at or below −40° C. Upon completion of addition, the reaction mixture was stirred for 15 minutes at −40° C. The reaction mixture was poured into ice (200 ml) and extracted with methylene chloride (7×40 ml). The extracts were combined, washed with water (2×40 ml), dried (magnesium sulfate) and concentrated under reduced pressure. The residue was passed through a column of silica gel eluting with ethyl acetate:heptane (1:9). Appropriate fractions were combined and concentrated under reduced pressure, yielding 1.07 g of 4-chloro-5-ethoxymethyl-2fluoronitrobenzene. The ir spectrum was consistent with the proposed structure.

Step C

Synthesis of 4-chloro-5-ethoxymethyl-2-fluoroaniline

A solution of 4-chloro-5-ethoxymethyl-2-fluoronitrobenzene (0.9 g, 0.0039 mole) in glacial acetic acid (50 ml) was added to a 250 ml Parr bottle containing platinum IV oxide (0.3 g) under a nitrogen atmosphere. The Parr bottle was placed on a Parr hydrogenation apparatus and charged with hydrogen. The reaction mixture was allowed to shake until hydrogen absorption ceased. The catalyst was removed by vacuum filtration. The 4-chloro-5-ethoxymethyl-2-fluoroaniline produced was used in the next step in acetic acid solution without being isolated.

Step D

Synthesis of
N-[4-chloro-2-fluoro-5-ethoxymethylphenyl]-3,4,5,6-tetrahydrophthalimide Tetrahydrophthalic anhydride (0.58 g, 0.0039 mole), and 4-chloro-5-ethoxymethyl-2-fluoroaniline in glacial acetic acid from Step C was heated at 100° C. overnight. Acetic acid was removed under reduced pressure. The residue was dissolved in ethyl acetate (100 ml) and washed successively with a saturated aqueous solution of sodium bicarbonate (5×50 ml) and a 10% aqueous solution of hydrochloric acid. The dried (magnesium sulfate) organic layer was concentrated under reduced pressure. The residue was passed through a column of silica gel eluting with ethyl acetate:heptane (3:17). Appropriate fractions were combined and concentrated under reduced pressure yielding N-[4-chloro-2-fluoro-5-ethoxymethylphenyl]-3,4,5,6-tetrahydrophthalimide as an amber solid, m.p. 89°–91° C. The nmr spectrum was consistent for the proposed structure.

EXAMPLE 2

Synthesis of N-[4-Chloro-2-Fluro-5-(1-Methoxyethylphenyl]-3,4,5,6-Tetrahydrophthalimide

Step A

Synthesis of 2-chloro-4-fluorobenzal bromide

In a flask were placed 150 g (1.04 moles) of 2-chloro-4-fluorotoluene, 391 g (2.20 moles) of N-bromosuccinimide, 3 g (0.012 mole) of benzoyl peroxide, and 800 ml of carbon tetrachloride. This mixture was refluxed overnight and then filtered. The solvent was evaporated under reduced pressure, leaving a residue of impure 2-chloro-4-fluorobenzal bromide weighing 340 g.

Step B

Synthesis of 2-chloro-4-fluorobenzaldehyde

In a flask were placed 30.25 g (0.100 mole) of 2-chloro-4-fluorobenzal bromide, 45 ml (1.2 mole) of formic acid, and 15 ml of concentrated hydrochloric acid. This mixture was heated at 100°–105° C. overnight. After cooling to room temperature, the reaction mixture was poured into 200 ml of an ice/water mixture which was then extracted twice with diethyl ether. The combined extracts were washed successively with a saturated, aqueous, sodium bicarbonate solution and water. After being dried over anhydrous magnesium sulfate, the extract was filtered, and the solvent was evaporated under reduced pressure, leaving 17 g of 2-chloro-4-fluorobenzaldehyde as a residue.

Step C

Synthesis of 1-(2-chloro-4-fluorophenyl)-ethanol

A solution of 5.25 g (0.033 mole) of 2-chloro-4-fluorobenzaldehyde in 100 ml of diethyl ether was cooled to −10° C., and 11.2 ml (0.033 mole) of a 2.95M solution of methylmagnesium bromide in diethyl ether was added dropwise with stirring. The reaction mixture was warmed to 0° C. and was stirred for several hours. After warming to room temperature, the reaction mixture was poured into an ice/water mixture. The resulting mixture was extracted with methylene chloride. The solvent was evaporated from the extract under reduced pressure, and the residue was passed through a column of silica gel, eluting first with heptane and then with ethyl acetate/heptane (1/9). The appropriate fractions were combined, and the solvent was evaporated under reduced pressure, leaving 1.46 g of 1-(2-chloro-4-fluorophenyl)ethanol as an amber oil. The nmr and ir spectra were consistent with the proposed structure. This reaction was repeated on a larger scale to provide sufficient 1-(2-chloro-4-fluorophenyl)ethanol for Step D.

Step D

Synthesis of 1-(2-chloro-4-fluoro-5-nitrophenyl)ethyl nitrate

A solution of 176 ml of fuming nitric acid in 25 ml of 1,2-dichloroethane was cooled to −20° C. To this solution was added dropwise a solution of 20 g (0.15 mole) of 1-(2-chloro-4-fluorophenyl)ethanol in 25 ml of 1,2-dichloroethane. During the addition which required 45 minutes, the reaction mixture temperature was maintained between −24° C. and −20° C. Stirring was continued at this temperature for 15 minutes following completion of addition, and then 150 ml of methylene chloride was added to the reaction mixture. After warming slowly to 0° C., the reaction mixture was slowly poured into an ice/water mixture. The organic phase was separated from the aqueous phase, and the latter was extracted four times with 50 ml of methylene chloride. The organic phase and the extracts were combined and were washed successively twice with cold water and three times with a cold, aqueous solution of sodium bicarbonate. The organic phase was dried over anhydrous magnesium sulfate, filtered, and the solvent was evaporated under reduced pressure, yielding 26 g of 1-(2-chloro-4-fluoro-5-nitrophenyl)ethyl nitrate as a residue. The nmr and ir spectra were consistent with the proposed structure.

Step E

Synthesis of 1-(2-chloro-4-fluoro-5-methylcarbonylaminophenyl)ethyl nitrate

In a Parr hydrogenation apparatus were placed 3.7 g (0.014 mole) of 1-(2-chloro-4-fluoro-5-nitrophenyl)ethyl nitrate, 0.35 g of platinum oxide catalyst, 35 ml of ethyl acetate, and 10 ml of acetic anhydride. The apparatus was pressurized with hydrogen, and the reaction was allowed to continue until the pressure ceased dropping. The reaction mixture was filtered, and the filtrate was concentrated under reduced pressure leaving a residue. This residue was mixed with 15 ml of water and 5 ml of 10% hydrochloric acid. This mixture was stirred at room temperature for two hours. Following dilution with water, the mixture was extracted with methylene chloride. The extracts were combined and washed successively with water, 5% hydrochloric acid, and a saturated, aqueous solution of sodium bicarbonate. This solution was dried, filtered, and the solvent was evaporated under reduced pressure leaving a residue. This residue was passed through a column of silica gel, eluting first with ethyl acetate/heptane (1/4) and then with ethyl acetate/heptane (1/1). The appropriate fractions were collected, and the solvent was evaporated under reduced pressure yielding 1.7 g of 1-(2-chloro-4-fluoro-5-methylcarbonylaminophenyl)ethyl nitrate as a white solid. The nmr and ir spectra were consistent with the proposed structure.

Step F

Synthesis of N-[4-chloro-2-fluoro-5-(1-methoxyethyl)phenyl]acetamide

To a clear, colorless solution of 0.4 g (0.0015 mole) of 1-(2-chloro-4-fluoro-5-methylcarbonylaminophenyl- )ethyl nitrate in 15 ml of absolute methanol was added dropwise 0.31 g (0.0015 mole) of a 25 weight percent solution of sodium methoxide in methanol. The reaction mixture turned pale yellow immediately and was stirred at room temperature for 2.5 hours. An additional 0.31 g (0.0015 mole) of the sodium methoxide solution was added, and stirring at room temperature continued for 18 hours. The mixture was heated at reflux for 2.5 hours and then was allowed to cool to room temperature. To the mixture was added 100 ml of diethyl ether, and this mixture was washed with water. The diethyl ether solution was dried, filtered, and the solvent was evaporated under reduced pressure, yielding 0.28 g of N-[4-chloro-2-fluoro-5-(1-methoxyethyl)phenyl]acetamide. The nmr and ir spectra were consistent with the proposed structure. This reaction was repeated to provide sufficient starting material for Step G.

Step G

Synthesis of 4-chloro-2-fluoro-5-(1-methoxyethyl)aniline

A mixture of 0.6 g (0.0024 mole) of N-[4-chloro-2-fluoro-5-(1-methoxyethyl)phenyl]acetamide, 0.14 g (0.0025 mole) of potassium hydroxide, 10 ml of water, and 10 ml of methanol was heated at reflux for 24 hours. This mixture was cooled and diluted with 50 ml of water. The resulting mixture was extracted successively with methylene chloride and diethyl ether. The combined extracts were dried, filtered, and the solvent was evaporated under reduced pressure, leaving 0.58 g of 4-chloro-2-fluoro-5-(1-methoxyethyl)aniline as an oil. The nmr spectrum was consistent with the proposed structure.

Step H

Synthesis of N-[4-chloro-2-fluoro-5-(1-methoxyethyl)phenyl]-3,4,5,6-tetrahydrophthalimide A mixture of 0.58 g (0.0029 mole) of 4-chloro-2-fluoro-5-(1-methoxyethyl)aniline, 0.82 g (0.0054 mole) of tetrahydrophthalic anhydride, and 15 ml of acetic acid was refluxed overnight. The acetic acid was then evaporated under reduced pressure, leaving a residue which was dissolved in diethyl ether. This solution was washed successively with water and an aqueous solution of sodium bicarbonate. The solution was dried, filtered, and the solvent was evaporated under reduced pressure leaving a residue. This residue was passed through a silica gel column, eluting with ethyl acetate/heptane (1/4). Appropriate fractions were combined, and the solvent was evaporated under reduced pressure, yielding 0.4 g of N-[4-chloro-2-fluoro-5-(1-methoxyethyl)phenyl]-3,4,5,6-tetrahydrophthalimide as a solid, m.p. 141°–44° C. The nmr and ir spectra were consistent with the proposed structure.

Analysis for $C_{17}H_{17}NClFO_3$ Calc'd: C 60.45; H 5.07; N 4.15; Found: C 60.29; H 5.11; N 3.94.

EXAMPLE 3

Synthesis of N-[4-Chloro-2-Fluoro-5-(Methylcarbonyloxymethyl)phenyl]-3,4,5,6-Tetrahydrophthalimide

Step A

Synthesis of 2-chloro-4-fluoro-5-nitrobenzaldehyde

To 300 ml of 1,2-dichloroethane that had been cooled to 0° C. was added 31.3 g (0.197 mole) of 2-chloro-4-fluorobenzaldehyde, prepared by the method of Example 2, Steps A and B. Subsequently, 19.96 g (0.197 mole) of potassium nitrate was added to the reaction mixture, and dropwise addition of 300 ml of concentrated sulfuric acid followed while maintaining the temperature between 0° C. and 5° C. The reaction was complete after 80 minutes, and 750 ml of methylene chloride was added to the reaction mixture. The phases were separated, and the sulfuric acid phase was extracted three times with 150 ml of methylene chloride. The extracts were combined with the organic phase before being washed three times with 450 ml of water. The extracts were dried over anhydrous magnesium sulfate, filtered, and the solvent was evaporated under reduced pressure, leaving an amber oil weighing 32.5 g as a residue. This oil was passed through a column of silica gel, eluting with ethyl acetate/heptane (1/4). The appropriate fractions were combined, and the solvent was evaporated under reduced pressure, leaving 26.0 g of 2-chloro-4-fluoro-5-nitrobenzaldehyde as an amber oil.

Step B

Synthesis of 2-chloro-4-fluoro-5-nitrobenzyl alcohol

To a solution of 10.8 g (0.053 mole) of 2-chloro-4-fluoro-5-nitrobenzaldehyde in 100 ml of tetrahydrofuran was added 0.50 g (0.013 mole) of sodium borohydride portionwise. The reaction mixture was stirred for one hour after which dilute hydrochloric acid was added to destroy unreacted sodium borohydride. To this mixture was added 200 ml of methylene chloride, and the phases were separated. The organic phase was washed three times with water, dried over anhydrous magnesium sulfate, and filtered. The solvent was evaporated from the filtrate under reduced pressure, leaving a residue weighing 10.7 g. This residue was combined with 1.67 g of a similar residue another run of the same reaction. The combined residues were passed through a silica gel column, eluting with ethyl acetate/heptane (1/4) to yield 7.7 g of 2-chloro-4-fluoro-5-nitrobenzyl alcohol as a yellow solid.

Step C

Synthesis of 2-chloro-4-fluoro-5-aminobenzylalcohol

In a Parr hydrogenation apparatus were placed 6.5 g (0.032 mole) of 2-chloro-4-fluoro-5-nitrobenzyl alcohol, 0.3 g of platinum oxide catalyst, and 100 ml of glacial acetic acid. Hydrogenation required 1.5 hours after which the catalyst was removed by filtration and the solvent was evaporated under reduced pressure, leaving 5.42 g of 2-chloro-4-fluoro-5-aminobenzyl alcohol as a tan solid. The nmr and ir spectra were consistent with the proposed structure.

Step D

Synthesis of N-[4-chloro-2-fluoro-5-(methylcarbonyloxymethyl)phenyl]-3,4,5,6-tetrahydrophthalimide A mixture of 4.9 g (0.028 mole) of 2-chloro-4-fluoro-5-aminobenzyl alcohol, 4.25 g (0.028 mole) of tetrahydrophthalic anhydride, and 100 ml of tetrahydrofuran was refluxed overnight. The solvent was evaporated under reduced pressure, leaving a thick, black oil. To this residue was added 100 ml of acetic acid, and the mixture was heated at 100° C. for several hours. The solvent was evaporated under reduced pressure and was replaced with 200 ml of ethyl acetate. This solution was washed three times with 150 ml of a saturated, aqueous solution of sodium bicarbonate and three times with 150 ml of 10% hydrochloric acid. The solution was dried over anhydrous magnesium sulfate, filtered, and the solvent was evaporated under reduced pressure, leaving 8.80 g of a viscous, black oil. This oil was passed through a column of silica gel, eluting with ethyl acetate/heptane (7/13). The appropriate fractions were combined, and the solvent was evaporated under reduced pressure, yielding 6.3 g of N-[4-chloro-2-fluoro-5-(methylcarbonyloxymethyl)phenyl]-3,4,5,6-tetrahydrophthalimide as a thick, amber oil. The nmr and ir spectra were consistent with the proposed structure.

Analysis for $C_{15}H_{13}ClFNO_3$ Calc'd: C 58.05; H 4.30; N 3.98; Found: C 57.27; H 3.96; N 3.45.

EXAMPLE 4

Synthesis of
N-(4-Chloro-2-Fluoro-5-Hydroxy-Methylphenyl)-3,4,5,6-Tetrahydrophthalimide In a flask were placed 3.5 g (0.0099 mole) of N-[4-chloro-2-fluoro-5-(methylcarbnyloxymethyl)phenyl]-3,4,5,6-tetrahydrophthalimide, 105 drops of concentrated hydrochloric acid, and 250 ml of absolute methanol. This mixture was stirred for approximately four hours after which the solvent was evaporated under reduced pressure. The residue was dissolved in 600 ml of diethyl ether. This solution was washed four times with 60 ml of water, dried over anhydrous magnesium sulfate, and filtered. The solvent was evaporated under reduced pressure, leaving an amber gum weighing 3.1 g as a residue. This residue was passed through a silica gel column, eluting with ethyl acetate/heptane (3/7). The appropriate fractions were combined, and the solvent was evaporated under reduced pressure, yielding 2.2 g of N-(4-chloro-2-fluoro-5-hydroxymethylphenyl)-3,4,5,6-tetrahydrophthalimide as a yellow solid, m.p. 135°–137° C. The nmr and ir spectra Were consistent with the proposed structure.

EXAMPLE 5

Synthesis of
N-[4-Chloro-2-Fluoro-5-(Phenylaminocarbonyloxymethyl)Phenyl-3,4,5,6-Tetrahydrophthalimide A mixture of 0.5 g (0.0016 mole) of N-(4-chloro-2-fluoro-5-hydroxymethylphenyl)-3,4,5,6-tetrahydrophthalimide, 0.66 g (0.0055 mole) of phenyl isocyanate, 0.73 g (0.0072 mole) of triethylamine, and 25 ml of methylene was stirred at room temperature overnight. Sufficient methanol was added to react with the excess phenyl isocyanate, and the reaction mixture was stirred for an additional 24 hours. The reaction mixture was diluted with ethyl acetate and was washed successively with water and 5% hydrochloric acid. The organic phase was dried, filtered, and the solvent was evaporated under reduced pressure. The residue was passed through a column of silica gel. The appropriate fractions were combined, and the solvent was evaporated under reduced pressure, leaving a white solid as a residue. This solid was recrystallized from ethyl acetate/heptane, yielding 0.29 g of N-[4-chloro-2-fluoro-5-(phenylaminocarbonyloxy)phenyl]-3,4,5,6-tetrahydrophthalimide as a white solid, m.p. 149°–151° C. The nmr and ir spectra were consistent with the proposed structure.

Analysis for $C_{22}H_{18}ClFN_2O_4$ Calc'd: C 61.62; H 4.23; N 6.53; Found: C 63.49; H 4.11; N 7.72.

EXAMPLE 6

Synthesis of
N-(4-Chloro-2-Fluoro-5-Phenoxymethylphenyl)-3,4,5,6-Tetrahydrophthalimide Step A Synthesis of
N-(4-chloro-2-fluoro-5-bromomethylphenyl)-3,4,5,6-tetrahydrophthalimide To a stirred solution of 3.0 g (0.0097 mole) of of N-(4-chloro-2-fluoro-5-hydroxymethylphenyl)-3,4,5,6-tetrahydrophthalimide, prepared by the method of Example 4, and 6.4 g (0.0194 mole) of carbon tetrabromide in 30 ml of diethyl ether was added portionwise 5.1 g (0.0194 mole) of triphenylphosphine. This mixture was stirred overnight and was then filtered to remove the solid which had formed, and the solvent was evaporated under reduced pressure. The residue was passed through a column of silica gel. Appropriate fractions were combined, and the solvent was evaporated yielding 1.1 g of N-(4-chloro-2-fluoro-5-bromomethylphenyl)-3,4,5,6tetrahydrophthalimide as a white solid, m .p. 126°–128° C. The nmr and ir spectra were consistent with the proposed structure.

Step B

Synthesis of
N-(4-chloro-2-fluoro-5-phenoxymethylphenyl)-3,4,5,6-tetrahydrophthalimide To a mixture of 0.6 g (0.0016 mole) of N-(4-chloro-2-fluoro-5-bromomethylphenyl)-3,4,5,6-tetrahydrophthalimide and 0.22 g (0.0016 mole) of potassium carbonate in acetone was added 0.15 g (0.0016 mole) of phenol. The mixture was stirred overnight at room temperature and then was heated at 50° C. for approximately 24 hours. The reaction mixture was filtered, and the filter cake was washed with ethyl acetate. The filtrate was washed with water, dried, and the solvent was evaporated under reduced pressure, leaving a residue weighing 0.7 g. Preparative thin layer chromatography was used to separate the components of this residue, eluting with ethyl acetate/heptane (3/7). The product, 0.18 g of N-(4-chloro-2-fluoro-5-phenoxymethylphenyl)-3,4,5,6-tetrahydrophthalimide, was isolated as an oil. The nmr and ir were consistent with the proposed structure.

EXAMPLE 7

Synthesis of
N-(4-Chloro-2-Fluoro-5-Diisopropylaminomethylphenyl)-3,4,5,6-Tetrahydrophthalimide Step A Synthesis of 2-chloro-4-fluoro-5-nitrotoluene To a mixture of 20.0 g (0.138 mole) of 2-chloro-4fluorotoluene in 50 ml of 1,2-dichloroethane which had been cooled to 0° C. was added 50 ml of concentrated sulfuric acid. While maintaining the temperature below 10° C., 14.0 g (0.138 mole) of potassium nitrate was added slowly to the mixture. After three hours the reaction mixture was poured into ice, and the resulting mixture was extracted with methylene chloride. The extract was dried over anhydrous magnesium sulfate, filtered, and the solvent was evaporated under reduced pressure. The residue was passed through a silica gel column, eluting with heptane. Appropriate fractions were combined, and the solvent was evaporated under reduced pressure, yielding 13.0 g of 2-chloro-4-fluoro-5-nitrotoluene as a yellow solid. The nmr spectrum was consistent with the proposed structure.

Step B

Synthesis of 2-chloro-4-fluoro-5-diacetylaminotoluene

In a Parr hydrogenator were placed 10 g (0.053 mole) of 2-chloro-4-fluoro-5-nitrotoluene, 0.39 g of platinum oxide catalyst, and 125 ml of ethyl acetate. The reaction vessel was pressurized with hydrogen. When the hydrogen pressure ceased dropping, the reaction mixture was stirred with magnesium sulfate and filtered. The solvent was evaporated under reduced pressure, and 100 ml of acetic anhydride was added to the residue. This mixture was heated overnight at 100° C. and then cooled to room temperature. After being poured into 300 ml of ice and stirring overnight, the mixture was extracted with methylene chloride. The extract was washed successively with water, an aqueous solution of sodium bicarbonate, and water. The extract was then dried, filtered, and the solvent was evaporated under reduced pressure, leaving a residue weighing 11 g. This residue was passed through a column of silica gel, eluting with ethyl acetate/heptane (1/4). Appropriate fractions were combined, and the solvent was evaporated under reduced pressure, yielding 7.8 g of 2-chloro-4-fluoro-5-diacetylaminotoluene.

Step C

Synthesis of 2-chloro-4-fluoro-5-diacetylaminobenzyl bromide

A mixture of 7.8 g (0.032 mole) of 2-chloro-4-fluoro-5-diacetylaminotoluene, 6.2 g (0.035 mole) of N-bromosuccinimide, 0.5 g of benzoyl peroxide, and 200 ml of carbon tetrachloride was heated at reflux for two days. This mixture was filtered, and the filtrate was washed with water. The filtrate was dried, and the solvent was evaporated under reduced pressure. The residue was passed through a column of silica gel, eluting with ethyl acetate/heptane (1/4). Appropriate fractions were combined, and the solvent was evaporated under reduced pressure, yielding 0.82 g of 2-chloro-4-fluoro-5-diacetylaminobenzyl bromide. The nmr was consistent with the proposed structure.

Step D

Synthesis of N,N-diisopropyl-2-chloro-4-fluoro-5-diacetylaminobenzylamine

A mixture of 0.82 g (0.0025 mole) of 2-chloro-4-fluoro-5-diacetylaminobenzyl bromide, 0.28 g (0.0028 mole) of diisopropylamine, 0.39 g (0.0028 mole) of potassium carbonate, and 25 ml of acetonitrile was heated at reflux overnight. The reaction mixture was diluted with ethyl acetate, and the resulting mixture was washed with water. After being dried, the solvent was evaporated under reduced pressure, yielding 0.82 g of N,N-diisopropyl-2-chloro-4-fluoro-5-diacetylaminobenzylamine.

Step E

Synthesis of 4-chloro-2-fluoro-5-(diisopropylaminomethyl)aniline

A mixture of 0.72 g (0.0021 mole) of N,N-diiso-propyl-2-chloro-4-fluoro-5-diacetylaminobenzylamine, 1 g (0.018 mole) of potassium hydroxide, 20 ml of methanol, and 5 ml of water was refluxed for six hours. After cooling to room temperature, the reaction mixture was diluted with diethyl ether and was washed with water. The aqueous washes were combined and extracted with methylene chloride. These extracts were combined with the diethyl ether solution. This mixture was dried, filtered, and the solvents were evaporated under reduced pressure, yielding 0.50 g of 4-chloro-2-fluoro-5-(diisopropylaminomethyl)aniline. The nmr and ir spectra were consistent with the proposed structure.

Step F

Synthesis of N-[4-chloro-2-fluoro-5-(diisopropylaminomethyl)-phenyl]-3,4,5,6-tetrahydrophthalimide By the method of Example 2, Step H, 0.50 g (0.0020 mole) of 4-chloro-2-fluoro-5-(diisopropylaminomethyl)aniline and 0.85 g (0.0056 mole) of tetrahydrophthalic anhydride in 20 ml of acetic acid were reacted yielding 0.052 g of N-[4-chloro-2-fluoro-5-(diisopropylaminomethyl)phenyl]-3,4,5,6-tetrahydrophthalimide. The nmr and ir spectra were consistent with the proposed structure.

EXAMPLE 8

Synthesis of N-[4-Chloro-2-Fluoro-5-[(4,4-Dimethyl-3-Oxoisoxazolidin-2-yl)-Methyl]Phenyl]-3,4,5,6-Tetrahydrophthalimide Step A Synthesis of 2-chloro-4-fluorobenzyl bromide By the method of Example 7, Step C, 141.4 g (0.978 mole) of 2-chloro-4-fluorotoluene, 175.8 g (0.978 mole) of N-bromosuccinimide, and 5.0 g of benzoyl peroxide in 15 liters of carbon tetrachloride were reacted, yielding 165 g of 2-chloro-4-fluorobenzyl bromide as a white solid.

Step B

Synthesis of 2-[(2-chloro-4-fluorophenyl)-methyl]-4,4-dimethyl-3-isoxazolidinone By the method of Example 6, Step B, 95.6 g (0.83 mole) of 4,4-dimethyl-3-isoxazolidinone, 186 g (0.83 mole) of 2-chloro-4-fluorobenzyl bromide, 114.7 g (0.83 mole) of potassium carbonate, and 2.2 g (0.008 mole) of 1,4,7,10,13,16-hexaoxacyclooctadecane were reacted at room temperature in 1500 ml of acetonitrile, yielding 230 g of impure 2-[(2-chloro-4-fluorophenyl)methyl]-4,4-dimethyl-3-isoxazolidinone. The nmr spectrum was consistent with the proposed structure.

Step C Synthesis of 2-[(2-chloro-4-fluoro-5-nitrophenyl)methyl]-4,4-dimethyl-3-isoxazolidinone By the method of Example 3, Step A, 20 g (0.078 mole) of 2-[(2-chloro-4-fluorophenyl)methyl]-4,4-dimethyl-3-isoxazolidinone, 7.8 g (0.78 mole) of potassium nitrate, and 100 ml of concentrated sulfuric acid were reacted, yielding 12 g of 2-[(2-chloro-4-fluoro-5-nitrophenyl)methyl]-4,4-dimethyl-3-isoxazolidinone as a light yellow solid. Passage through a column of silica gel was omitted since the product was crystalline. Purification was accomplished by recrystallization from ethyl acetate/hexane. This reaction was repeated, and the products were combined.

Step D

Synthesis of 2-[(2-chloro-4-fluoro-5-aminophenyl)methyl]-4,4-dimethyl-3-isoxazolidinone By the method of Example 3, Step C, 16.0 g (0.052 mole) of 2-[(2-chloro-4-fluoro-5-nitrophenyl)methyl]-4,4-dimethyl-3-isoxazolidinone was hydrogenated in the presence of 0.2 g of platinum oxide in 250 ml of ethanol, yielding 2-[(2-chloro-4-fluoro-5-aminophenyl)methyl]-4,4-dimethyl-3-isoxazolidinone.

Step E

Synthesis of N-[4-chloro-2-fluoro-5-[(4,4-dimethyl-3-oxoisoxazolidin-2-yl)methyl]-phenyl]-3,4,5,6-tetrahydrophthalimide By the method of Example 2, Step H, 3.0 g (0.011 mole) of 2-[(2-chloro-4-fluoro-5-aminophenyl)methyl-4,4-dimethyl-3-isoxazolidinone and 1.84 g (0.012 mole) of tetrahydrophthalic anhydride were reacted in 10 ml of acetic acid, yielding 3.0 g of N-[4-chloro-2-fluoro-5[(4,4-dimethyl-3-oxoisoxazolidin-2-yl)methyl]phenyl]-3,4,5,6-tetrahydrophthalimide as a yellow solid, m.p. 136°–138° C. The nmr and ir spectra were consistent with the proposed structure.

Analysis for $C_{20}H_{20}ClFN_2O_4$ Calc'd: C 59.04; H 4.96; N 6.89; Found: C 59.18; H 4.70; N 6.66.

EXAMPLE 9

Synthesis of N-[4-Chloro-2-Fluoro-5-(N-Methyl-N-Methylsulfonylaminomethyl)Phenyl]-3,4,5,6-Tetrahydrophthalimide

Step A

Synthesis of N-methyl-N-(2-chloro-4-fluorobenzyl)methylsulfonamide

By the method of Example 6, Step B, 10.0 g (0.045 mole) of 2-chloro-4-fluorobenzyl bromide, prepared by the method of Example 8, Step A, 4.88 g (0.045 mole) of N-methylmethylsulfonamide, 6.18 g (0.045 mole) of potassium carbonate, and 0.50 g (0.0019 mole) of 1,4,7,10,13,16-hexaoxacyclooctadecane Were reacted in 125 ml of acetonitrile. This mixture was refluxed overnight. The solid product, N-methyl-N-(2-chloro-4-fluorobenzyl)methylsulfonamide, weighed 6.95 g, m.p. 88°–90° C. The nmr and ir spectra were consistent with the proposed structure.

Step B

Synthesis of N-methyl-N-(2-chloro-4-fluoro-5-nitrobenzyl)methylsulfonamide

By the method of Example 2, Step D, 6.80 g (0.027 mole) of N-methyl-N-(2-chloro-4-fluorobenzyl)methylsulfonamide sulfonamide and 75 ml of fuming nitric acid were reacted in 50 ml of 1,2-dichloroethane, yielding 2.42 g of N-methyl-N-(2-chloro-4-fluoro-5-nitrobenzyl)methylsulfonamide as a white solid, m.p. 141°–42° C. The nmr and ir spectra were consistent with the proposed structure.

Step C

Synthesis of N-methyl-N-(2-chloro-4-fluoro-5-aminobenzyl)methylsulfonamide

By the method of Example 3, Step C, 1.0 g (0.0034 mole) of N-methyl-N-(2-chloro-4-fluoro-5-nitrobenzyl)methylsulfonamide was hydrogenated in the presence of 0.3 g of platinum oxide in 90 ml of glacial acetic acid, yielding 0.75 g of N-methyl-N-(2-chloro-4-fluoro-5aminobenzyl)methylsulfonamide as a yellow-tan solid, m.p. 108°–109° C. The nmr spectrum was consistent with the proposed structure.

Step D

Synthesis of N-[4-chloro-2-fluoro-5-(N-methyl-N-methylsulfonylaminomethyl)phenyl]-3,4,5,6-tetrahydrophthalimide By the method of Example 2, Step H, 0.75 g (0.0021 mole) of N-methyl-N-(2-chloro-4-fluoro-5-aminobenzyl)methylsulfonamide and 0.33 g (0.0021 mole) of tetrahydrophthalic anhydride were reacted in 100 ml of glacial acetic acid , yielding 0.15 g of N-[4-chloro-2-fluoro-5-(N-methyl-N-methylsulfonylaminomethyl)-phenyl]-3,4,5,6-tetrahydrophthalimide.

EXAMPLE 10

Synthesis of N-(4-Bromo-2-Fluro-5-Ethoxymethylphenyl)-3,4,5,6-Tetrahydrophthalimide

Step A

Synthesis of 2-bromo-4-fluorobenzyl bromide

By the method of Example 7, Step C, 75 g (0.40 mole) of 2-bromo-4-fluorotoluene, 70.6 g (0.40 mole) of N-bromosuccinimide, and 2.5 g (0.03 mole) of benzoyl peroxide were reacted in 450 ml of carbon tetrachloride, yielding 107.8 g of impure 2-bromo-4-fluorobenzyl bromide (68% assay).

Step B

Synthesis of ethyl 2-bromo-4-fluorobenzyl ether

By the method of Example 1, Step A, 10.9 g (0.041 mole) of 2-bromo-4-fluorobenzyl bromide and 18.2 ml of a 21% by weight solution of sodium ethoxide in ethanol were reacted in 50 ml of tetrahydrofuran, yielding 7.18 g of ethyl 2-bromo-4-fluorobenzyl ether.

Step C

Synthesis of ethyl 2-bromo-4-fluoro-5-nitrobenzyl ether

By the method of Example 2, Step D, 7.18 g (0.0308 mole) of ethyl 2-bromo-4-fluoro benzyl ether, 2 ml of fuming nitric acid, and 18 ml of concentrated sulfuric acid were reacted in 20 ml of 1,2-dichloroethane, yielding 3.1 g of ethyl 2-bromo-4-fluoro-5-nitrobenzyl ether.

Step D

Synthesis of ethyl 2-bromo-4-fluoro-5-aminobenzyl ether

To a flask containing 50 ml of glacial acetic acid heated to 80° C. was added 4 g (0.07 mole) of iron powder. This was followed by the dropwise addition of a solution of 2 g (0.007 mole) of ethyl 2-bromo-4-fluoro-5-nitrobenzyl ether in 60 ml of acetic acid while maintaining the temperature between 80° C. and 85° C. After 30 minutes the reaction mixture was cooled to room temperature and was filtered. The solvent was evaporated under reduced pressure, and the residue was dissolved in 250 ml of diethyl ether. This solution was washed successively twice with 50 ml of water, once with 50 ml of a saturated, aqueous solution of sodium bicarbonate, and twice with 50 ml of water. The solution was dried over anhydrous magnesium sulfate, filtered, and the solvent was evaporated under reduced pressure, yielding 1.51 g of ethyl 2-bromo-4-fluoro-5-aminobenzyl ether. An additional 0.1 g of product was obtained by extracting the water washes with diethyl ether.

Step E

Synthesis of N-(4-bromo-2-fluoro-5-ethoxymethylphenyl)-3,4,5,6-tetrahydrophthalimide By the method of Example 2, Step H, 1.61 g (0.00649 mole) of ethyl 2-bromo-4-fluoro-5-aminobenzyl ether and 1.08 g (0.0071 mole) of tetrahydrophthalic anhydride were reacted in 30 ml of glacial acetic acid, yielding 1.01 g of N-(4-bromo-2-fluoro-5-ethoxymethylphenyl)-3,4,5,6-tetrahydrophthalimide as a yellow solid, m.p. 104°–106° C. The nmr and ir spectra were consistent with the proposed structure.

Analysis for $C_{17}H_{17}BrFNO_3$ Calc'd: C 54.42; H 4.48; N 3.66; Found: C 53.45; H 4.16; N 3.53.

EXAMPLE 11

Synthesis of N-[5-(N-Acetyl-N-Methoxyamino)Methyl-4-Chloro-2-Fluorophenyl]-3,4,5,6-Tetrahydrophthalimide Step A Synthesis of N-(2-chloro-4-fluorobenzyl)-N-methoxyacetamide To a stirred mixture of 1.95 g (0.0219 mole) of N-methoxyacetamide, 1.23 g 0.022 mole) of powdered potassium hydroxide, and a small amount (~0.05 g) of 18-crown-6 in 10 ml of tetrahydrofuran was added a solution of 5.05 g (0.0226 mole) of 4-fluoro-2-chlorobenzyl bromide in 15 ml of tetrahydrofuran. This mixture was heated at reflux for approximately 17 hours and then was allowed to cool to room temperature. The mixture was diluted with 125 ml of diethyl ether and was washed with an aqueous, saturated sodium chloride solution. The organic phase was dried over anhydrous magnesium sulfate and filtered. The filtrate was evaporated under reduced pressure leaving a yellow oil. This oil was purified by column chromatography on silica gel, eluting with ethyl acetate:n-heptane (25:75) followed by ethyl acetate:n-heptane (50:50), to yield 1.7 g of N-(2-chloro-4-fluoro-benzyl)-N-methoxyacetamide as an oil.

The nmr and ir spectra were consistent with the proposed structure.

Step B

Synthesis of N-(2-chloro-4-fluoro-5-nitrobenzyl)-N-methoxyacetamide

The nitration of 1.59 g (0.00685 mole of N-(2-chloro-4-fluorobenzyl)-N-methoxyacetamide with 0.45 ml of fuming nitric acid and 4 ml of concentrated sulfuric acid in 10 ml of 1,2-dichloroethane produced 1.51 g of N-(2-chloro-4-fluoro-5-nitrobenzyl)-N-methoxyacetamide as a solid, m.p. 94°–95° C.

The nmr and ir spectra were consistent with the proposed structure.

Step C

Synthesis of 5-[(N-acetyl-N-methoxyamino)-methyl]-4-chloro-2-fluoroaniline

N-(2-chloro-4-fluoro-5-nitrobenzyl)-N-methoxyacetamide (1.1 g, 0.0040 mole) was hydrogenated with a small amount (0.1 g) of platinum oxide in 50 ml of acetic acid. The reaction mixture was filtered to leave a solution of 5-[(N-acetyl-N-methoxyamino)methyl]-4-chloro-2-fluoroaniline (0.98 g) dissolved in 50 ml of acetic acid.

Step D

Synthesis of N-[5-(N-acetyl-N-methoxyamino)-methyl-4-chloro-2-fluorophenyl]-3,4,5,6-tetrahydrophthalimide A stirred mixture of 37.2 ml of the solution prepared in Step C and 0.66 g (0.0044 mole) of 3,4,5,6-tetrahydrophthalic anhydride was heated at reflux for approximately 16 hours. The mixture was allowed to cool to room temperature. The solvent was removed by distillation under reduced pressure leaving a residue. This residue was dissolved in 100 ml of diethyl ether. The organic solution was washed first with 25 ml of an aqueous, saturated sodium bicarbonate solution followed by three 25 ml water washes. The washed organic solution was dried over anhydrous magnesium sulfate and was filtered. The filtrate was evaporated under reduced pressure leaving an orange oil. This oil was purified by column chromatography on silica gel, eluting with ethyl acetate:n-heptane (1:1) followed by ethyl acetate, to yield 0.89 g of N-[5-(N-acetyl-N-methoxyamino)-methyl-4-chloro-4-fluorophenyl]-3,4,5,6-tetrahydrophthalimide as an oil.

The nmr and ir spectra were consistent with the proposed structure

Analysis $C_{18}H_{18}ClFN_2O_4$; Calc'd: C 56.77; H 4.76; N 7.36; Found: C 58.32; H 5.13; N 7.62.

HERBICIDAL ACTIVITY

The plant test species used in demonstrating the herbicidal activity of compounds of this invention include cotton (*Gossvoium hirsutum* var. Stoneville), soybean (*Glvcine max* var. Williams), field corn (*Zea mavs* var. Agway 595S), wheat (*Triticum aestivium* var. Prodax), rice (*Orvza sativa*), field bindweed (*Convolvulus arvensis*), morningglory (*Ipomea lacumosa* or *Ipomea hederacea*), wild mustard (*Brassica kaber*), velvetleaf (*Abutilon theophrasti*), barnyardgrass (*Echinochloa crus galli*), green foxtail (*Setaria viridis*), and johnsongrass (*Sorohum haleoense*).

Seeds or tubers of the plant test species were planted in furrows in steam sterilized sandy loam soil contained in disposable fiber flats. A topping soil of equal portions of sand and sandy loam soil was placed uniformly on top of each flat to a depth of approximately 0.5 cm.

The flats for the preemergence test were watered, then drenched with the appropriate amount of a solution of the test compound in a 50/50 mixture of acetone and water containing a small amount (up to 0.5% v/v) of sorbitan monolaurate emulsifier/solubilizer. The concentration of the test compound in solution was varied to give a range of application rates, generally 8.0 kg/ha and submultiples thereof. The flats were placed in a greenhouse and watered regularly at the soil surface for 21 days at which time phytotoxicity data were recorded.

The flats for the postemergence test were placed in a greenhouse and watered for 8-10 days, then the foliage of the emerged test plants was sprayed with a solution of the test compound in acetone-water containing up to 0.5% sorbitan monolaurate. After spraying, the foliage was kept dry for 24 hours, then watered regularly for 21 days, and phytotoxicity data recorded.

Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The present rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | Satisfactory to good weed control |
| 90 | | Only occasional live plants left | Very good to excellent control |
| 100 | Complete effect | Complete crop destruction | Complete weed destruction |

Tests of the effectiveness of weed control of paddy rice were done in pots containing clay loam paddy soil under water maintained at a depth of 3 cm. In one test tubers of narrowleaf arrowhead (*Sagittaria pymaea*) and rhizomes of flatsedge (*Cyperus serotinus*) were planted in pots at depth of 2 cm and 0.5 cm respectively, rice seedlings of 2.2 leaf stage were transplanted in depth of 2 cm and 0 cm and a controlled amount of a 10% wp (wettable powder) formulation of the herbicidal compound in water was dropped into the water over the soil at 1 dry and 11 days, respectively, after transplanting. In another test, seeds of various weed species (including barnyardgrass, *Echinochoa crus-galli;* smallflower umbrellaplant, *Cyperus difformis;* bulrush, *Scripus juncoides;* Japanese ducksalad, *Monochoria vaginalis;* annual broadleaf weeds; and narrowleaf waterplantain, *Alisma canaliculatium*) were sown on the surface of the soil and the same (1 day and 11 day) herbicide applications were made. In tests of compound I (of Table 1 below) very high activity against weeds of wide spectrum were shown for both the 1 day and 11 day treatments at rates (e.g., 0.03 kg/ha) which gave little or no phytotoxicity to rice transplanted at a depth of 2 cm.

Herbicidal data at selected application rates are given for various compounds of the invention in Tables 3 and 4 below. The test compounds are identified in the tables of herbicidal data below by numbers which correspond to those used in Table 1 below.

In the Tables of herbicidal data below "kg/ha" is kilograms per hectare.

For herbicidal application, the active compounds as above defined are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, watersoluble or water-dispersible granules, as powdery dusts, as wettable powders, as emulsifiable concentrates, as solutions or as any of several other known types of formulations, depending on the desired mode of application.

For preemergence application these herbicidal compositions are usually applied either as sprays, dusts, or granules to the areas in which suppression of vegetation is desired. For postemergence control of established plant growth, sprays or dusts are most commonly used. These formulations may contain as little as 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part of the herbicidal compound and 99.0 parts of talc.

Wettable powders, also useful formulations for both pre- and postemergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, and 1.0 part of sodium lignosulfonate and 0.3 part of sulfonate aliphatic polyester as wetting agents. Frequently, additional wetting agent and/or oil will be added to the tank-mix for postemergence application to facilitate dispersion on the foliage and absorption by the plant.

Other useful formulations for herbicidal applications are emulsifiable concentrates. Emulsifiable concentrates are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Typical wetting, dispersing or emulsifying agents used in agricultural formulations include, for example, the alkyl and alkylaryl sulfonates and sulfates and their sodium salts; polyhydric alcohols; and other types of surface active agents, many of which are available in commerce. The surface active agent, when used, normally comprises 1% to 15% by weight of the herbicidal composition.

Other useful formulations for herbicidal applications include simple solutions of the active ingredient in a dispersant in which it is completely soluble at the desired concentration, such as acetone, alkylated naphthalenes, xylene or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442, incorporated herein by reference, are useful herein with the present herbicidal compounds.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, for example, 7 g/ha or lower.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl)-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3-H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]-amino-2-methyl-propanenitrile (cyanazine); dinitroaniline herbicides such as 2,6-dinitro-N,N-dipropyl-4-(trifluoromethyl)-benzeneamine (trifluralin); and aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention, without departing from the inventive concepts herein, as defined in the claims which follow.

TABLE 1

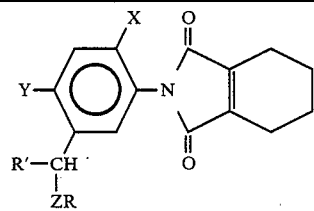

| Cmpd. No. | X | Y | R' | Z | R | R² |
|---|---|---|---|---|---|---|
| 1 | F | Cl | H | O | ethyl | |
| 2 | F | Cl | H | O | methyl | |
| 3 | F | Cl | H | O | n-propyl | |
| 4 | F | Cl | H | O | isopropyl | |
| 5 | F | Cl | H | O | n-butyl | |
| 6 | F | Cl | H | O | $CH_2CH_2F$ | |
| 7 | F | Br | H | O | ethyl | |
| 8 | Cl | Cl | H | O | ethyl | |
| 9 | F | Br | H | O | isopropyl | |
| 10 | F | Cl | $CH_3$ | O | ethyl | |
| 11 | F | Cl | $CH_3$ | O | isopropyl | |
| 12 | F | Cl | $CH_3$ | O | methyl | |
| 13 | F | $CF_3$ | H | O | ethyl | |
| 14 | Br | Cl | H | O | ethyl | |
| 15 | Cl | Cl | H | O | $CH_2C(O)OCH_3$ | |
| 16 | F | Cl | H | O | phenyl | |
| 17 | F | Cl | H | O | 4-methoxyphenyl | |
| 18 | F | Cl | H | O | $C(O)CH_3$ | |
| 19 | F | Cl | H | O | $C(O)NHC_6H_5$ | |
| 20 | F | Cl | H | O | $CH_2C(O)OCH_3$ | |
| 21 | F | Cl | H | O | $CH_2C(O)OC_2H_5$ | |

TABLE 1-continued

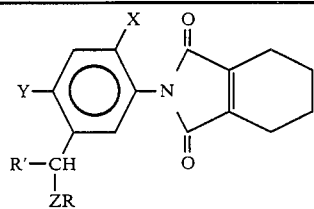

| Cmpd. No. | X | Y | R' | Z | R | $R^2$ |
|---|---|---|---|---|---|---|
| 22 | F | Cl | H | O | $CH_2C(O)OCH(CH_3)_2$ | |
| 23 | F | Cl | H | O | $CH_2C(O)OC_4H_9(n)$ | |
| 24 | F | Cl | H | S | methyl | |
| 25 | F | Cl | H | S | ethyl | |
| 26 | F | Cl | H | S(O) | ethyl | |
| 27 | F | Cl | H | $S(O)_2$ | ethyl | |
| 28 | F | Cl | H | $NR^2$ | ethyl | hydrogen |
| 29 | F | Cl | H | $NR^2$ | isopropyl | isopropyl |
| 30 | F | Cl | H | $NR^2$ | $S(O)_2CH_3$ | methyl |
| 31 | F | Cl | H | $NR^2$ | $CO_2CH_3$ | methoxy |
| 32 | F | Cl | H | $NR^2$ | $R-R^2 = -CH_2CH_2OCH_2CH_2-$ | |
| 33 | F | Cl | H | $NR^2$ | $R-R^2 = -C(O)C(CH_3)_2CH_2O-$ | |
| 34 | F | Br | $CH_3$ | O | ethyl | |
| 35 | F | Cl | $CH_3$ | O | n-propyl | |
| 36 | F | Cl | $CH_3$ | O | n-butyl | |
| 37 | F | Cl | $CH_3$ | O | phenyl | |
| 38 | F | Cl | $CH_3$ | O | benzyl | |
| 39 | F | Cl | $CH_3$ | S | methyl | |
| 40 | F | Cl | $CH_3$ | S | ethyl | |
| 41 | F | Cl | $CH_3$ | S | phenyl | |
| 42 | F | Cl | $C_2H_5$ | O | methyl | |
| 43 | F | Cl | $C_3H_7(n)$ | O | methyl | |
| 44 | Cl | Cl | $CH_3$ | O | methyl | |
| 45 | Cl | Br | $CH_3$ | O | methyl | |
| 46 | F | Br | $CH_3$ | O | methyl | |
| 47 | F | Cl | $CH_3$ | $NR^2$ | ethyl | hydrogen |
| 48 | F | Cl | $CH_3$ | $NR^2$ | phenyl | hydrogen |
| 49 | F | Cl | H | $NR^2$ | $C(O)CH_3$ | hydrogen |
| 50 | F | Cl | H | O | $CH_2C(O)OH$ | |
| 51 | F | Cl | H | O | $CH_2C(O)OC_6H_5$ | |
| 52 | F | Cl | H | O | $CH_2C(O)OCH_2C_6H_5$ | |
| 53 | F | Cl | H | O | $CH_2C(O)NH_2$ | |
| 54 | F | Cl | H | O | $CH_2C(O)NHC_2H_5$ | |
| 55 | F | Cl | H | O | $CH_2C(O)NHCH(CH_3)_2$ | |
| 56 | F | Cl | H | O | $CH_2C(O)NHC_6H_5$ | |
| 57 | F | Cl | H | O | $CH_2C(O)NHSO_2CH_3$ | |
| 58 | F | Cl | H | O | $CH_2C(O)NHSO_2C_6H_5$ | |
| 59 | F | Cl | H | O | $CH_2C(O)NHSO_2C_6H_4Cl(2)$ | |
| 60 | F | Cl | H | O | $CH_2C(O)NHSO_2C_6H_4OCH_3(4)$ | |
| 61 | F | Br | H | O | $CH_2C(O)OCH_3$ | |
| 62 | F | Cl | H | S | $CH_2C(O)OCH_3$ | |
| 63 | F | Cl | H | $NR^2$ | $CH_2C(O)OCH_3$ | hydrogen |
| 64 | F | Cl | H | S | $CH_2C(O)NHC_2H_5$ | |
| 65 | F | Cl | H | S | $CH_2C(O)NHSO_2CH_3$ | |
| 66 | F | Cl | H | S | $CH_2C(O)NHC_6H_5$ | |
| 67 | F | Cl | H | S(O) | $CH_2C(O)OCH_3$ | |
| 68 | F | Cl | H | $S(O)_2$ | $CH_2C(O)OCH_3$ | |
| 69 | F | Cl | H | $NR^2$ | $C(O)C_2H_5$ | methoxy |
| 70 | F | Cl | H | $NR^2$ | $C(O)C_3H_7(n)$ | methoxy |
| 71 | F | Cl | H | $NR^2$ | $C(O)CH_2Cl$ | methoxy |
| 72 | F | Cl | H | $NR^2$ | $C(O)CHCl_2$ | methoxy |
| 73 | F | Cl | H | $NR^2$ | $C(O)C(CH_3)_2CH_2Cl$ | methoxy |
| 74 | F | Cl | H | $NR^2$ | $C(O)CH_3$ | benzyloxy |
| 75 | F | Br | H | $NR^2$ | $C(O)CH_3$ | methoxy |
| 76 | F | $CHF_2O$ | H | O | ethyl | |
| 77 | F | Cl | H | O | $C(O)C_2H_5$ | |
| 78 | F | Cl | H | O | $C(O)CH_2Cl$ | |
| 79 | F | Cl | H | O | $C(O)CH_2F$ | |
| 80 | F | Cl | H | O | $C(O)CH_2CH_2Cl$ | |
| 81 | F | Cl | H | O | $CH(CH_3)C(O)OC_2H_5$ | |
| 82 | F | Cl | H | O | $CH_2C(O)OCH_2CH_2Cl$ | |
| 83 | F | Cl | H | O | $C(O)NHCH_3$ | |
| 84 | F | Cl | H | O | 2-chlorophenyl | |
| 85 | F | Cl | H | O | 4-chlorophenyl | |
| 86 | F | Cl | H | $NR^2$ | ethyl | ethyl |
| 87 | F | Cl | H | $NR^2$ | $C(O)CH_3$ | ethyl |
| 88 | F | Cl | H | $NR^2$ | $C(O)CH_3$ | methoxy |
| 89 | F | Cl | H | $S(O)_2$ | methyl | |

TABLE 1-continued

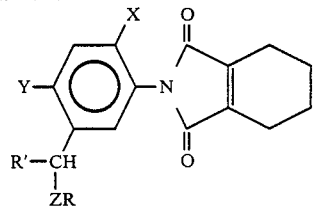

| Cmpd. No. | X | Y | R' | Z | R | R² |
|---|---|---|---|---|---|---|
| 90 | F | Cl | H | S(O) | methyl | |

TABLE 2

| Compound No. | M.P. (°C.) | Elemental Analysis | | | | Empirical Formula |
|---|---|---|---|---|---|---|
| | | | C | H | N | |
| 1 | 89–91 | C | 60.45 | 5.07 | 4.15 | C₁₇H₁₇ClFNO₃ |
| | | F | 58.30 | 5.00 | 4.03 | |
| 2 | 90–92 | C | 59.36 | 4.67 | 5.44 | C₁₆H₁₅ClFNO₃ |
| | | F | 58.92 | 4.42 | 4.40 | |
| 3 | Oil | C | 61.45 | 5.44 | 3.98 | C₁₈H₁₉ClFNO₃ |
| | | F | 60.08 | 5.45 | 3.89 | |
| 5 | Oil | C | 62.38 | 5.79 | 3.83 | C₁₉H₂₁ClFNO₃ |
| | | F | 62.19 | 5.63 | 3.76 | |
| 6 | 107–108 | C | 57.39 | 4.53 | 3.94 | C₁₇H₁₆ClF₂NO₃ |
| | | F | 56.11 | 4.61 | 3.88 | |
| 7 | 104–106 | C | 54.42 | 4.48 | 3.66 | C₁₇H₁₇BrFNO₃ |
| | | F | 53.45 | 4.16 | 3.53 | |
| 8 | 116–118 | C | 57.64 | 4.84 | 3.95 | C₁₇H₁₇Cl₂NO₃ |
| | | F | 57.35 | 4.95 | 4.10 | |
| 12 | 141–144 | C | 60.45 | 5.07 | 4.15 | C₁₇H₁₇ClFNO₃ |
| | | F | 60.29 | 5.11 | 3.94 | |
| 16 | Oil | | | | | C₂₁H₁₇ClFNO₃ |
| 17 | 147–149 | | | | | C₂₂H₁₉ClFNO₄ |
| 18 | Oil | C | 58.05 | 4.30 | 3.98 | C₁₇H₁₅ClFNO₃ |
| | | F | 57.27 | 3.96 | 3.45 | |
| 19 | 149–151 | C | 61.62 | 4.23 | 6.53 | C₂₂H₁₈ClFN₂O₄ |
| | | F | 63.49 | 4.11 | 7.72 | |
| 20 | 116–117 | | | | | C₁₈H₁₇ClFNO₅ |
| 21 | 78–80 | C | 57.65 | 4.84 | 3.54 | C₁₉H₁₉ClFNO₅ |
| | | F | 57.22 | 4.68 | 3.53 | |
| 22 | Oil | | | | | C₂₀H₂₁ClFNO₅ |
| 23 | Oil | | | | | C₂₁H₂₃ClFNO₅ |
| 24 | Oil | | | | | C₁₆H₁₅ClFNO₂S |
| 25 | Oil | | | | | C₁₇H₁₇ClFNO₂S |
| 27 | 137–140 | | | | | C₁₇H₁₇ClFNO₄S |
| 28 | Oil | C | 60.63 | 5.39 | 8.32 | C₁₇H₁₈ClFN₂O₂ |
| | | F | 58.69 | 5.65 | 7.78 | |
| 29 | Oil | | | | | C₂₁H₂₆ClFN₂O₂ |
| 30 | Oil | | | | | C₁₇H₁₈ClFN₂O₄S |
| 32 | 118–119 | C | 60.24 | 5.32 | 7.39 | C₁₉H₂₀ClFN₂O₃ |
| | | F | 59.94 | 5.10 | 7.49 | |
| 33 | 136–138 | C | 59.04 | 4.96 | 6.89 | C₂₀H₂₀ClFN₂O₄ |
| | | F | 59.18 | 4.70 | 6.66 | |
| 86 | Oil | C | 62.55 | 6.08 | 7.68 | C₁₉H₂₂ClFN₂O₂ |
| | | F | 62.51 | 5.99 | 7.60 | |
| 87 | Oil | | | | | C₁₉H₂₀ClFN₂O₃ |
| 88 | Oil | C | 56.77 | 4.76 | 7.36 | C₁₈H₁₈ClFN₂O₄ |
| | | F | 58.32 | 5.13 | 7.62 | |
| 89 | 159–162 | | | | | C₁₆H₁₅ClFNO₄S |
| 90 | Oil | | | | | C₁₆H₁₅ClFNO₃S |

TABLE 3

Preemergence Evaluation (% Control)

| | Compound No. | | | |
|---|---|---|---|---|
| | 1 | 2 | 3 | 5 |
| | Rate (kg/ha) | | | |
| Species | 1.0 | 1.0 | 0.5 | 0.5 |
| Cotton | 60 | 40 | 50 | 30 |
| Soybean | 70 | 30 | 20 | 20 |
| Field Corn | 70 | 20 | 10 | 10 |
| Rice | 80 | 70 | 20 | 20 |
| Wheat | 80 | 80 | 40 | 10 |
| Field Bindweed | 100 | 100 | 100 | 100 |
| Morningglory | 100 | 80 | 100 | 90 |
| Wild Mustard | — | — | — | — |
| Velvetleaf | 100 | 100 | 100 | 95 |
| Barnyardgrass | 100 | 100 | 95 | 50 |
| Green Foxtail | 100 | 95 | 100 | 95 |
| Johnsongrass | 100 | 100 | 95 | 90 |

| | Compound No. | | | |
|---|---|---|---|---|
| | 6 | 7 | 8 | 12 |
| | Rate (kg/ha) | | | |
| Species | 1.0 | 1.0 | 1.0 | 1.0 |
| Cotton | 90 | 30 | 30 | 40 |
| Soybean | 70 | 70 | 10 | 50 |
| Field Corn | 60 | 60 | 5 | 40 |
| Rice | 80 | 50 | 10 | 50 |
| Wheat | 90 | 60 | 10 | 40 |
| Field Bindweed | 100 | — | — | — |
| Morningglory | 100 | 100 | 40 | 90 |
| Wild Mustard | — | 100 | 70 | 100 |
| Velvetleaf | 100 | 100 | 100 | 100 |
| Barnyardgrass | 100 | 90 | 60 | 100 |
| Green Foxtail | 100 | 100 | 100 | 100 |
| Johnsongrass | 95 | 80 | 30 | 90 |

| | Compound No. | | | |
|---|---|---|---|---|
| | 16 | 17 | 18 | 19 |
| | Rate (kg/ha) | | | |
| Species | 0.5 | 1.0 | 1.0 | 1.0 |
| Cotton | 0 | 10 | 60 | 0 |
| Soybean | 0 | 10 | 20 | 0 |
| Field Corn | 0 | 0 | 10 | 0 |
| Rice | 0 | 20 | 50 | 10 |
| Wheat | 0 | 20 | 50 | 0 |
| Field Bindweed | — | — | 95 | 30 |
| Morningglory | 10 | 30 | 60 | 0 |
| Wild Mustard | 30 | 80 | — | — |
| Velvetleaf | 50 | 100 | 100 | 10 |
| Barnyardgrass | 0 | 50 | 50 | 10 |

| | Compound No. | | | |
|---|---|---|---|---|
| | 20 | 21 | 22 | 23 |
| | Rate (kg/ha) | | | |
| Species | 1.0 | 0.5 | 1.0 | 1.0 |
| Cotton | 0 | 0 | 10 | 10 |
| Soybean | 0 | 0 | 10 | 0 |
| Field Corn | 50 | 0 | 0 | 0 |
| Rice | 50 | 20 | 20 | 10 |
| Wheat | 20 | 0 | 0 | 0 |
| Field Bindweed | 95 | 60 | — | — |
| Morningglory | 90 | 40 | 40 | 50 |
| Wild Mustard | — | — | 0 | 0 |
| Velvetleaf | 70 | 20 | 20 | 20 |
| Barnyardgrass | 20 | 20 | 10 | 0 |
| Green Foxtail | 20 | 0 | 0 | 0 |
| Johnsongrass | 30 | 30 | 0 | 0 |

| | Compound No. | | | |
|---|---|---|---|---|
| | 24 | 25 | 27 | 28 |
| | Rate (kg/ha) | | | |
| Species | 1.0 | 1.0 | 1.0 | 1.0 |

TABLE 3-continued

Preemergence Evaluation (% Control)

| | | | | |
|---|---|---|---|---|
| Cotton | 70 | 90 | 60 | 0 |
| Soybean | 40 | 80 | 80 | 5 |
| Field Corn | 60 | 80 | 80 | 5 |
| Rice | 60 | 80 | 80 | 20 |
| Wheat | 50 | 70 | 70 | 0 |
| Field Bindweed | — | — | — | — |
| Morningglory | 90 | 100 | 100 | 10 |
| Wild Mustard | 100 | 100 | 100 | 5 |
| Velvetleaf | 100 | 100 | 100 | 80 |
| Barnyardgrass | 95 | 100 | 95 | 0 |
| Green Foxtail | 90 | 100 | 95 | 5 |
| Johnsongrass | 95 | 95 | 95 | 0 |

| | Compound No. | | | |
|---|---|---|---|---|
| | 30 | 32 | 33 | 86 |
| | Rate (kg/ha) | | | |
| Species | 1.0 | 1.0 | 2.0 | 1.0 |
| Cotton | 50 | 20 | 100 | 5 |
| Soybean | 20 | 20 | 100 | 10 |
| Field Corn | 40 | 80 | 50 | 0 |
| Rice | 40 | 95 | 70 | 5 |
| Wheat | 60 | 80 | 50 | 0 |
| Field Bindweed | — | — | 100 | — |
| Morningglory | 70 | 90 | 100 | 50 |
| Wild Mustard | 100 | 100 | — | 40 |
| Velvetleaf | 100 | 100 | 100 | 70 |
| Barnyardgrass | 95 | 95 | 100 | 20 |
| Green Foxtail | 70 | 100 | 100 | 95 |

| | Compound No. | | | |
|---|---|---|---|---|
| | 87 | 88 | 89 | 90 |
| | Rate (kg/ha) | | | |
| Species | 1.0 | 1.0 | 1.0 | 1.0 |
| Cotton | 90 | 70 | 50 | 50 |
| Soybean | 70 | 100 | 30 | 20 |
| Field Corn | 70 | 70 | 80 | 40 |
| Rice | 70 | 70 | 50 | 50 |
| Wheat | 90 | 70 | 50 | 50 |
| Field Bindweed | — | — | — | — |
| Morningglory | 90 | 100 | 90 | 100 |
| Wild Mustard | 100 | 100 | 100 | 100 |
| Velvetleaf | 100 | 100 | 100 | 100 |
| Barnyardgrass | 100 | 95 | 80 | 70 |
| Green Foxtail | 100 | 100 | 60 | 80 |
| Johnsongrass | 95 | 95 | 80 | 80 |

TABLE 4

Postemergence Evaluation (% Control)

| | Compound No. | | | |
|---|---|---|---|---|
| | 1 | 2 | 3 | 5 |
| | Rate (kg/ha) | | | |
| Species | 1.0 | 1.0 | 0.5 | 0.5 |
| Cotton | 100 | 100 | 95 | 100 |
| Soybean | 100 | 90 | 100 | 95 |
| Field Corn | 50 | 50 | 70 | 80 |
| Rice | 80 | 90 | 80 | 50 |
| Wheat | 100 | 100 | 40 | 40 |
| Field Bindweed | 100 | 100 | 95 | 100 |
| Morningglory | 100 | 100 | 100 | 90 |
| Wild Mustard | — | — | — | — |
| Velvetleaf | 100 | 100 | 100 | 100 |
| Barnyardgrass | 100 | 100 | 60 | 60 |
| Green Foxtail | 100 | 100 | 100 | 100 |
| Johnsongrass | 100 | 95 | 100 | 80 |

| | Compound No. | | | |
|---|---|---|---|---|
| | 6 | 7 | 8 | 12 |
| | Rate (kg/ha) | | | |
| Species | 1.0 | 1.0 | 1.0 | 1.0 |
| Cotton | 100 | 100 | 100 | 100 |
| Soybean | 90 | 70 | 70 | 100 |
| Field Corn | 100 | 60 | 40 | 60 |
| Rice | 90 | 90 | 30 | 70 |
| Wheat | 100 | 70 | 20 | 90 |
| Field Bindweed | 100 | — | — | — |
| Morningglory | 100 | 100 | 90 | 90 |

TABLE 4-continued

Postemergence Evaluation (% Control)

| | | | | |
|---|---|---|---|---|
| Wild Mustard | — | 100 | 70 | 100 |
| Velvetleaf | 100 | 100 | 100 | 100 |
| Barnyardgrass | 95 | 90 | 0 | 80 |
| Green Foxtail | 100 | 95 | 30 | 100 |
| Johnsongrass | 90 | 80 | 20 | 80 |

| | Compound No. | | | |
|---|---|---|---|---|
| | 16 | 17 | 18 | 19 |
| | Rate (kg/ha) | | | |
| Species | 0.5 | 1.0 | 1.0 | 1.0 |
| Cotton | 100 | 100 | 100 | 40 |
| Soybean | 20 | 40 | 30 | 30 |
| Field Corn | 20 | 30 | 10 | 10 |
| Rice | 20 | 20 | 40 | 10 |
| Wheat | 20 | 30 | 50 | 20 |
| Field Bindweed | — | — | 95 | 20 |
| Morningglory | 60 | 50 | 100 | 50 |
| Wild Mustard | 80 | 20 | — | — |
| Velvetleaf | 100 | 90 | 100 | 90 |
| Barnyardgrass | 10 | 30 | 20 | 30 |
| Green Foxtail | 80 | 20 | 30 | 70 |

| | Compound No. | | | |
|---|---|---|---|---|
| | 20 | 21 | 22 | 23 |
| | Rate (kg/ha) | | | |
| Species | 1.0 | 0.5 | 1.0 | 1.0 |
| Cotton | 100 | 100 | 100 | 100 |
| Soybean | 90 | 60 | 80 | 70 |
| Field Corn | 80 | 20 | 50 | 40 |
| Rice | 95 | 40 | 90 | 50 |
| Wheat | 100 | 100 | 95 | 80 |
| Field Bindweed | 100 | 100 | — | — |
| Morningglory | 100 | 60 | 100 | 100 |
| Wild Mustard | — | — | 100 | 100 |
| Velvetleaf | 100 | 100 | 100 | 100 |
| Barnyardgrass | 70 | 90 | 70 | 90 |
| Green Foxtail | 90 | 100 | 90 | 100 |
| Johnsongrass | 100 | 50 | 50 | 60 |

| | Compound No. | | | |
|---|---|---|---|---|
| | 24 | 25 | 27 | 28 |
| | Rate (kg/ha) | | | |
| Species | 1.0 | 1.0 | 1.0 | 1.0 |
| Cotton | 100 | 100 | 90 | 80 |
| Soybean | 80 | 80 | 95 | 95 |
| Field Corn | 40 | 70 | 40 | 50 |
| Rice | 50 | 70 | 60 | 20 |
| Wheat | 70 | 95 | 60 | 20 |
| Field Bindweed | — | — | — | — |
| Morningglory | 100 | 100 | 100 | 100 |
| Wild Mustard | 100 | 100 | 100 | 100 |
| Velvetleaf | 100 | 100 | 100 | 100 |
| Barnyardgrass | 70 | 100 | 100 | 10 |
| Green Foxtail | 95 | 100 | 95 | 70 |
| Johnsongrass | 80 | 100 | 80 | 10 |

| | Compound No. | | | |
|---|---|---|---|---|
| | 29 | 30 | 32 | 33 |
| | Rate (kg/ha) | | | |
| Species | 1.0 | 1.0 | 1.0 | 2.0 |
| Cotton | 100 | 100 | 80 | 100 |
| Soybean | 50 | 80 | 90 | 90 |
| Field Corn | 40 | 30 | 90 | 100 |
| Rice | 40 | 50 | 90 | 90 |
| Wheat | 40 | 50 | 95 | 100 |
| Field Bindweed | — | — | — | 100 |
| Morningglory | 100 | 100 | 100 | 90 |
| Wild Mustard | 100 | 100 | 100 | — |
| Velvetleaf | 100 | 100 | 100 | 100 |
| Barnyardgrass | 70 | 40 | 100 | 100 |
| Green Foxtail | 95 | 80 | 100 | 100 |

| | Compound No. | | | |
|---|---|---|---|---|
| | 86 | 87 | 88 | 89 |
| | Rate (kg/ha) | | | |
| Species | 1.0 | 1.0 | 1.0 | 1.0 |
| Cotton | 95 | 100 | 100 | 100 |
| Soybean | 80 | 95 | 100 | 100 |

TABLE 4-continued

| Postemergence Evaluation (% Control) | | | | |
|---|---|---|---|---|
| Field Corn | 40 | 70 | 70 | 40 |
| Rice | 50 | 80 | 70 | 40 |
| Wheat | 40 | 70 | 70 | 70 |
| Field Bindweed | — | — | — | — |
| Morningglory | 100 | 100 | 100 | 100 |
| Wild Mustard | 100 | 100 | 100 | 100 |
| Velvetleaf | 100 | 100 | 100 | 100 |
| Barnyardgrass | 60 | 90 | 100 | 95 |
| Green Foxtail | 50 | 95 | 100 | 100 |
| Johnsongrass | 50 | 90 | 100 | 90 |

| | Compound No. |
|---|---|
| | 90 |
| | Rate (kg/ha) |
| Species | 1.0 |
| Cotton | 100 |
| Soybean | 70 |
| Field Corn | 40 |
| Rice | 50 |
| Wheat | 90 |
| Field Bindweed | — |
| Morningglory | 100 |
| Wild Mustard | 100 |
| Velvetleaf | 100 |
| Barnyardgrass | 80 |
| Green Foxtail | 95 |
| Johnsongrass | 80 |

I claim:

1. A herbicidal compound of the formula

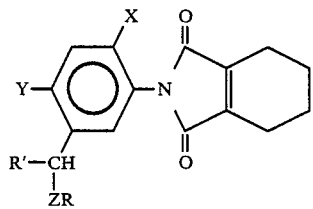

where X is F, Cl or Br; Y is Cl, Br, $CHF_2O$ or $CF_3$; Z is O, S, S(O), $S(O)_2$ or $NR^2$; R is alkyl, lower halo alkyl, aryl, aralkyl, alkylcarbonyl, haloalkylcarbonyl, alkoxy- or haloalkoxycarbonylalkyl, alkyl- or haloalkyl- or arylaminocarbonyl carboxyalkyl, aryloxycarbonylalkyl, aralkyloxycarbonylalkyl, aminocarbonylalkyl, lower alkylaminocarbonylalkyl, arylaminocarbonylalkyl, alkylsulfonylaminocarbonylalkyl or arylsulfonylaminocarbonylalkyl; R', is H or lower alkyl; and $R^2$ is hydrogen, lower alkyl, lower alkoxy or aralkyloxy; and wherein any aryl moiety is monocyclic and any alkyl moiety has 1 to 6 carbon atoms.

2. A compound as in claim 1 in which Z is O.

3. A compound as in claim 1 in which Z is S, S(O) or $S(O)_2$.

4. A compound as in claim 1 in which Z is $NR^2$.

5. A compound as in claim 2 in which R is ethyl.

6. A compound as in claim 5 in which X is F, Y is Cl, and R' is H.

7. A compound as in claim 3 in which X is F, Y is Cl or Br and R' is H.

8. A compound as in claim 4 in which X is F, Y is Cl or Br and R' is H.

9. A herbicidal composition containing an herbicidally effective amount of a compound of claim 1 in admixture with a suitable carrier.

10. A herbicidal composition containing an herbicidally effective amount of a compound of claim 6 in admixture with a suitable carrier.

11. A method of controlling weeds which comprises applying to the locus where control is desired an herbicidally effective amount of the composition of claim 9.

12. A method of controlling weeds which comprises applying to the locus where control is desired an herbicidally effective amount of the composition of claim 10.

13. The method of claim 12 wherein the locus where control is desired is planted with soybeans, corn, rice or wheat.

14. The method of claim 12 wherein the locus where control is desired is planted with soybeans.

15. The method of claim 12 wherein said locus is planted with paddy rice.

* * * * *